US00PP33040P2

(12) United States Plant Patent
Diessenbacher

(10) Patent No.: US PP33,040 P2
(45) Date of Patent: May 11, 2021

(54) ***PAULOWNIA* TREE NAMED 'WEGROW-B7'**

(50) Latin Name: ***Paulownia* hybrid**
Varietal Denomination: WEGROW-B7

(71) Applicant: WeGrow GmbH, Tonisvorst (DE)

(72) Inventor: Peter Diessenbacher, Tonisvorst (DE)

(73) Assignee: WeGrow GmbH, Tonisvorst (DE)

( * ) Notice: Subject to any disclaimer, the term of this patent is extended or adjusted under 35 U.S.C. 154(b) by 0 days.

(21) Appl. No.: 16/907,394

(22) Filed: Jun. 22, 2020

(51) Int. Cl.
*A01H 5/04* (2018.01)
*A01H 6/00* (2018.01)

(52) U.S. Cl.
USPC ..... Plt./216

(58) Field of Classification Search
USPC ..... Plt./216
CPC ..... A01H 5/00; A01H 5/04; A01H 6/00
See application file for complete search history.

*Primary Examiner* — June Hwu
(74) *Attorney, Agent, or Firm* — Samuel R. McCoy, Jr.

(57) ABSTRACT

A new and distinct *Paulownia* hybrid tree named 'WEGROW-B7' which is characterized by a fast rate of growth, developing a large diameter trunk in a relatively short period of time, an upright trunk with a narrow canopy, and high frost tolerance. The claimed plant propagates successfully by softwood stem cuttings and has proven to be uniform and stable in the resulting generations.

3 Drawing Sheets

Latin name of the genus and species: The Latin name of the genus and species of the novel variety disclosed herein is *Paulownia* hybrid.

Variety denomination: The inventive variety of *Paulownia* hybrid disclosed herein has been given the variety denomination 'WEGROW-B7'.

BACKGROUND OF THE INVENTION

Parentage: The claimed tree is a spontaneous whole-plant mutation of an unnamed and unpatented *Paulownia elongata* x *Paulownia fortunei* hybrid plant which was discovered by the inventor in the summer of 2012 at a commercial tree farm in Bonn, Germany. The mutation was noted for its fast rate of growth, near vertical trunk and narrow foliar canopy.

Asexual Reproduction: In the summer of 2012, 'WEGROW-B7' was first asexually reproduced by way of meristematic tissue culture micropropagation in Bonn, Germany. The claimed tree was found to asexually reproduce in uniform and stable manner and 6 successive cycles of vegetative propagation have proven to be true to type.

SUMMARY OF THE INVENTION

The following characteristics have been repeatedly observed and represent the distinguishing characteristics of the new *Paulownia* tree, 'WEGROW-B7'. These traits, in combination, distinguish 'WEGROW-B7' as a new and distinct cultivar.

1. 'WEGROW-B7' exhibits an upright trunk with a narrow canopy which, in cultivation for timber production, equates to a higher planting density and a lesser pruning requirement; and
2. 'WEGROW-B7' develops a large diameter trunk in a relatively short period of time which, in cultivation for timber production, equates to a relatively short production cycle; and 3. 'WEGROW-B7' exhibits large, medium green leaves; and
4. 'WEGROW-B7' exhibits frost tolerance to minus ten degrees Celsius.

BOTANICAL DESCRIPTION OF THE PLANT

Figure 1:
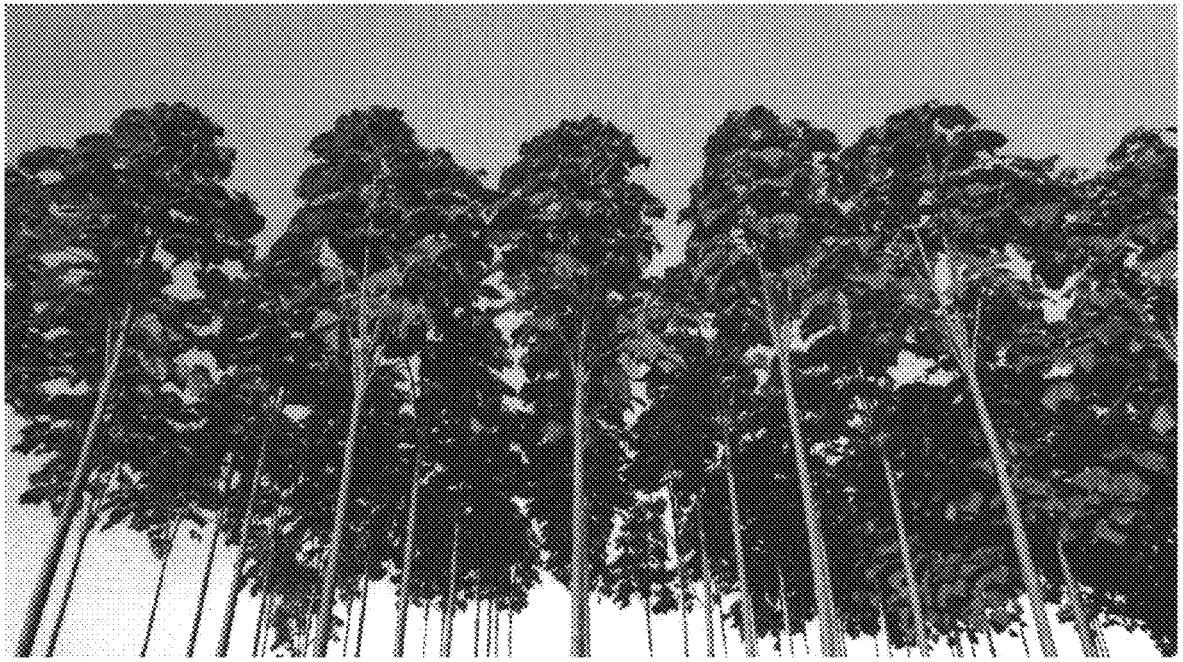
FIG. 1 illustrates, as nearly true as it is reasonably possible to make the same in color photographs of this type, a field-grown 'WEGROW-B7' tree at approximately 3.5 years of age, during spring in Tonisvorst, Germany.
Figure 2:
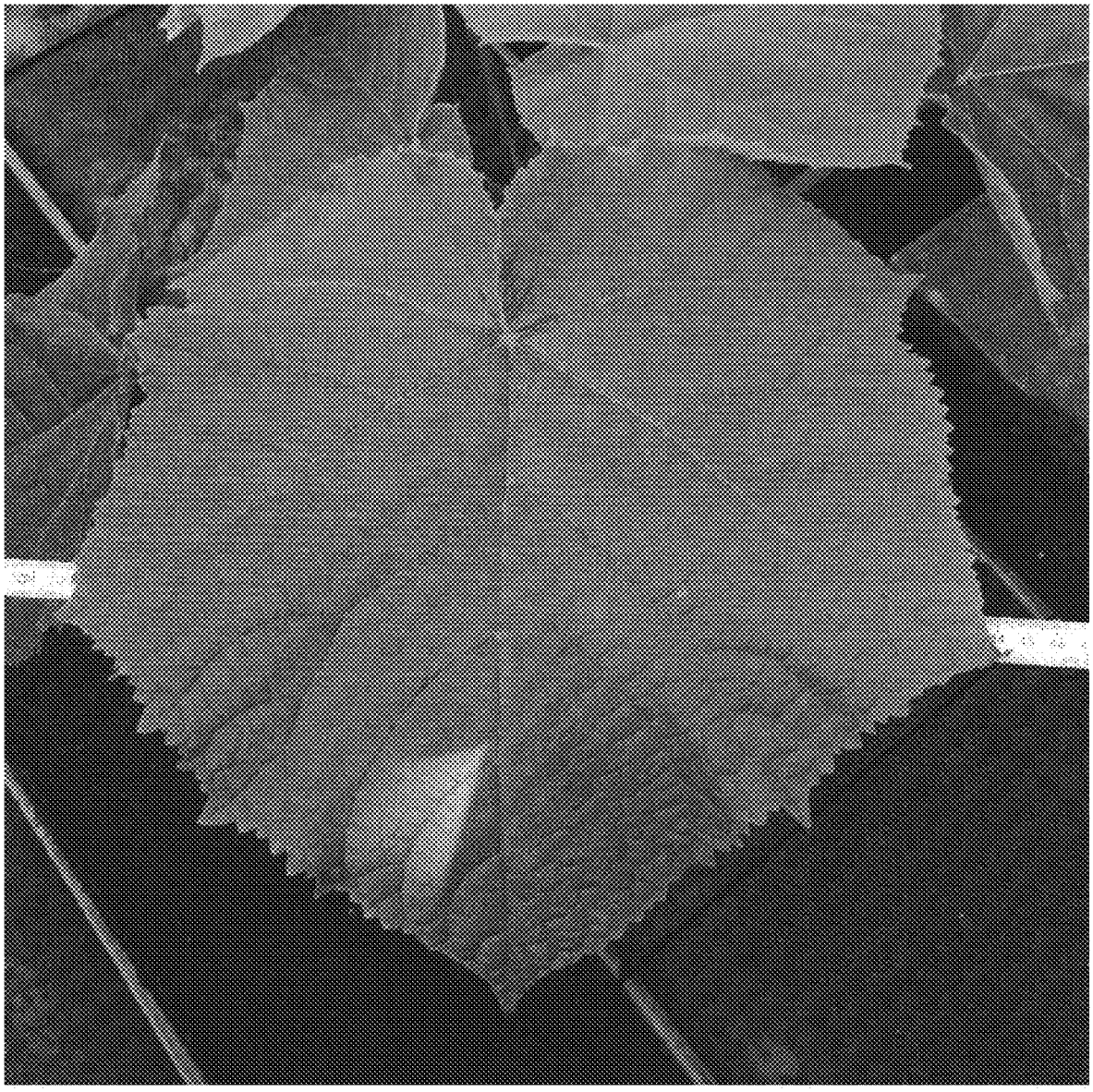
FIG. 2 illustrates, as nearly true as it is reasonably possible to make the same in color photographs of this type, the exemplary mature foliage of 'WEGROW-B7'.
Figure 3:
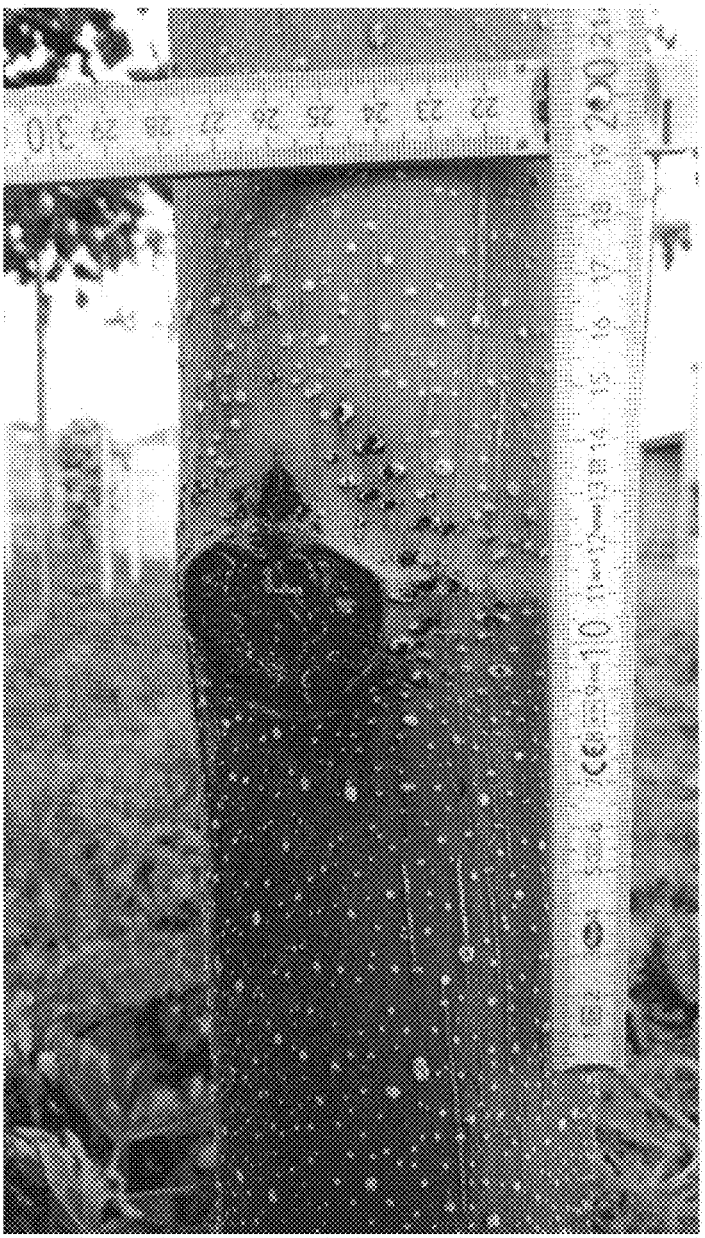
FIG. 3 illustrates, as nearly true as it is reasonably possible to make the same in color photographs of this type, the oldest wood of a mature field-grown 'WEGROW-B7' tree.

The following is a detailed botanical description of a new and distinct *Paulownia* hybrid plant known as 'WEGROW-B7'. Plant observations were made on a 3.5 year-old field-grown tree in Tonisvorst, Germany. The observed tree was grown in full exposure to natural sunlight, and maintained with drip irrigation. No pest or pathogen countermeasures were employed. Two years after planting the observed tree into the field, the tree was pruned to the soil level in May of 2018 and allowed to regrow for approximately 1.5 years. Observation data was then recorded in November of 2019.

Those skilled in the art will appreciate that certain characteristics will vary with older or, conversely, younger plants. 'WEGROW-B7' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on *The Royal Horticultural Society Colour Chart*, The Royal Horticultural Society, London, 2015 (sixth edition).

A botanical description of 'WEGROW-B7' and comparisons with the parent and most similar commercial cultivar are provided below.

General plant description:

*Plant habit*.—Deciduous tree with an upright ascending, moderately branching growth habit.

*Tree canopy profile*.—Rotund.

*Dimensions*.—The original tree grew to approximately 7.75 meters tall and 2.25 meters wide.

*Plant vigor*.—Very vigorous.

*Growth rate*.—Very fast growing.

*Environmental tolerances*.—Cold hardy to at least minus −10 degrees Celsius; prefers well drained soils with regular irrigation, and full sun exposure.

*Pest and disease susceptibility or resistance*.—Plants have not been observed to be susceptible or resistant to pathogens and pests common to *Paulownia* sp.

*Propagation*.—Propagation is accomplished by way of meristematic tissue culture micropropagation.

*Crop time*.—When cultivated for timber production, approximately five growing seasons are needed to first harvest and an additional two seasons for main harvest.

Root system:

*Description*.—A network of fibrous, non-fleshy roots.

*Rooting habit*.—Freely branching, moderately dense, and relatively shallow in the soil profile.

Stems:

*Branching habit*.—A dominant, near-vertical central main stem, typically unbranched, gives rise to unbranched lateral branches. Main stem; central leader — Quantity — One. Attitude — Erect; near vertical. Aspect — Generally rounded. Diameter — 12.0 cm, at breast height. Strength — Very strong. Texture — Glabrous, lenticellate and becoming progressively fissured with age. Lenticels are irregularly elliptical to elliptical and range in size from 0.5 mm to 5.0 mm long and 1.0 to 5.0 mm wide; color is greyed-green, nearest to in between RHS 197D and 199D. Color, juvenile — Greyed-green, nearest to a mixture of RHS 197B, 197C, and 197D; irregularly blotched and banded with greyed-green, nearest to RHS 196B. Moderately suffused with a mixture of green, RHS 144A, and yellow-green, RHS 146A; suffusion becomes less pronounced as the wood ages. Color, oldest wood — Brown, nearest to a mixture of RHS 199B, 200A, 200B, 200C and 200D; irregularly blotched and banded with greyed-green, nearest to RHS 196B; fissures are in nearest to in between yellow-green and greyed-orange, RHS 152A and 177B. Lateral branches — Quantity — 7.5, on average. Attitude — Very upright; very acute crotch angles. Aspect — Round. Diameter — 7.0 cm at the base, on average. Stem strength — Strong. Texture and luster — Glabrous, moderately glossy, and moderately lenticellate. Lenticels are irregularly elliptical to elliptical and range in size from 1.0 mm to 5.0 mm long and 1.0 to 4.0 mm wide; color is greyed-green, nearest to in between RHS 197D and 198D. Color — Greyed-green, nearest to a mixture of RHS 199B, 199C, and 199D; irregularly blotched and banded with greyed-green, nearest to RHS 196B. Moderately suffused with a mixture of green, RHS 144A, and yellow-green, RHS 146D.

Foliage:

*Arrangement*.—Opposite.

*Attachment*.—Petiolate.

*Division*.—Simple.

*Shape*.—Broadly rhomboid to broadly cordate.

*Length*.—39.6 cm.

*Width*.—38.0 cm.

*Apex*.—Acuminate.

*Base*.—Lobate to sagitate.

*Margin*.—Ciliate; serrate to doubly serrate; slightly to moderately undulated.

*Aspect*.—Flat.

*Texture and pubescence, adaxial surface*.—Glabrous, slightly bullate, and slightly glossy.

*Texture and pubescence, abaxial surface*.—Pubescent, slightly bullate and matte.

*Color*.—Juvenile foliage, adaxial surface — Yellow-green, nearest to RHS 143A. Juvenile foliage, abaxial surface — Yellow-green, nearest to in between RHS 143A and 143B. Mature foliage, adaxial surface — Yellow-green, nearest to RHS 143A. Mature foliage, abaxial surface — Yellow-green, nearest to in between RHS 143A and 143B.

*Venation*.—Pattern — Palmate. Vein color, adaxial surface — Yellow-green, nearest to RHS 146D. Vein color, abaxial surface — Yellow-green, nearest to RHS 146C.

*Petiole*.—Length — 10.0 to 14.0 mm. Diameter — 0.6 to 1.0 cm. Texture, adaxial and abaxial surfaces — Moderately pubescent. Color — Yellow-green, nearest to a mixture of RHS 144A and N144A, and suffused with yellow-green, RHS 152A.

Inflorescence: To date, no flowering has been observed.

Flower bud: To date, no flowering has been observed.

Flower: To date, no flowering has been observed.

Reproductive organs: To date, no flowering has been observed.

Fruit and seed: To date, no fruiting has been observed.

COMPARISON WITH THE PRESUMED PARENT PLANT

Plants of the new cultivar 'WEGROW-B7' differ from the parent, an unnamed *Paulownia* hybrid tree (not patented), by the characteristics described in Table 1.

TABLE 1

| Characteristic | 'WEGROW-B7' | The parent |
|---|---|---|
| Tree height. | Taller than the parent. | Shorter than 'WEGROW-B7'. |
| Growth rate. | Faster growing than the parent. | Slower growing than 'WEGROW-B7'. |
| General coloration of the foliage. | Lighter shade of green relative to the parent. | Darker shade of green compared to 'WEGROW-B7'. |

COMPARISON WITH THE MOST SIMILAR *PAULOWNIA* HYBRID CULTIVAR KNOWN TO THE INVENTOR

Plants of the new cultivar 'WEGROW-B7' are most similar to the commercial cultivar, *Paulownia* 'Phoenix One' (Community Plant Variety Rights grant number 39980). A comparison of 'WEGROW-B7' with *Paulownia* 'Phoenix One' is described in Table 2.

TABLE 2

| Characteristic | 'WEGROW-B7' | 'Phoenix One' |
|---|---|---|
| Rate of growth. | Faster than 'Phoenix One'. | Slower than 'WEGROW-B7'. |
| General coloration of the mature foliage. | Lighter shade of green compared to 'Phoenix One'. | Darker shade of green compared to 'WEGROW-B7'. |

TABLE 2-continued

| Characteristic | 'WEGROW-B7' | 'Phoenix One' |
|---|---|---|
| Width of tree canopy. | Narrower than 'Phoenix One'. | Wider than 'WEGROW-B7'. |

That which is claimed is:

1. A new and distinct variety of *Paulownia* hybrid tree named 'WEGROW-B7', substantially as described and illustrated herein.

* * * * *